(12) United States Patent
Kurth et al.

(10) Patent No.: US 7,355,200 B2
(45) Date of Patent: Apr. 8, 2008

(54) ION-SENSITIVE FIELD EFFECT TRANSISTOR AND METHOD FOR PRODUCING AN ION-SENSITIVE FIELD EFFECT TRANSISTOR

(75) Inventors: Eberhard Kurth, Moritzburg (DE); Christian Kunath, Dresden (DE); Heinrich Grüger, Dresden (DE)

(73) Assignee: Fraunhofer-Gasellschaft zur Forderung der angewandten Forschung e.V., Munich (DE)

(*) Notice: Subject to any disclaimer, the term of this patent is extended or adjusted under 35 U.S.C. 154(b) by 43 days.

(21) Appl. No.: 11/126,846

(22) Filed: May 10, 2005

(65) Prior Publication Data

US 2005/0263798 A1 Dec. 1, 2005

Related U.S. Application Data

(63) Continuation of application No. PCT/EP02/12785, filed on Nov. 14, 2002.

(51) Int. Cl.
*H01L 23/58* (2006.01)
(52) U.S. Cl. .......... 257/48; 257/E21.036; 257/E21.529
(58) Field of Classification Search ........ 257/382–412, 257/48; 438/287–305
See application file for complete search history.

(56) References Cited

U.S. PATENT DOCUMENTS 6,300,203 B1* 10/2001 Buynoski et al. .......... 438/287
6,399,208 B1 6/2002 Baum et al.
6,465,334 B1 10/2002 Buynoski et al.
6,479,404 B1 11/2002 Steigerwald et al.
2002/0109161 A1 8/2002 Chou et al.

FOREIGN PATENT DOCUMENTS

DE 44 30 811 8/1994
DE 195 14 251 4/1995

OTHER PUBLICATIONS

Abe, H., et al. "ISFET's Using Inorganic Gate Thin Films." IEEE Transactions on Electron Devices. USA. Dec. 1979.
Bergveld, P. "Development of an Ion-Sensitive Solid-State Device for Neurophysiological Measurements." Short Communications.
Klein, V., et al. "The ion-sensitive field-effect Transistor—a Semiconductor Sensor for Chemical Quanitites."
Sakai, T., et al. Ion Sensitive Fet with a Silicon-Insulator-Silicon Structure. Intl. Electron Devices Meeting. Tranducers '87.
Sobczyńska, D., et al. "$ZrO_2$ Gate pH-Sensitive Field Effect Transistor." Sensors and Actuators. Netherlands. 1984.
Van der Schoot, B., et al. "The ISFET in Analytical Chemistry." Sensors and Actuators. Netherlands. 1983.
Voight, H., et al. "Diamond-like Carbon-gate pH-ISFET." Sensors and Actuators. 1997.
Wilk, G.D., et al. "Hafrilium and Zirconium Silicates for Advanced Gate Dielectrics." Journal of Applied Physics. vol. 87, No. 1. Jan. 2000.

* cited by examiner

*Primary Examiner*—Cuong Nguyen
(74) *Attorney, Agent, or Firm*—Michael A. Glenn; Glenn Patent Group

(57) ABSTRACT

An ion-sensitive field effect transistor has a gate consisting of metal silicate. The gate of metal silicate provides high resistance to aggressive measured substances and further has a high long-term stability. The gate of the ion-sensitive field effect transistor may include a single layer gate, wherein the gate is arranged directly on the channel region.

3 Claims, 1 Drawing Sheet

ION-SENSITIVE FIELD EFFECT TRANSISTOR AND METHOD FOR PRODUCING AN ION-SENSITIVE FIELD EFFECT TRANSISTOR

CROSS-REFERENCE TO RELATED APPLICATION

This application is a continuation of copending International Application No. PCT/EP02/12785, filed on Nov. 14, 2002, which designated the United States and was not published in English.

BACKGROUND OF THE INVENTION

1. Field of the Invention

The present invention relates to field effect transistors and particularly to ion-sensitive field effect transistors as well as to a method for producing the same.

2. Description of the Related Art

Ion-sensitive field effect transistors (ISFET) serve as detection elements, for example in measuring a pH value, in measuring ionic concentrations or special substance concentrations in solutions of various compositions and conductivities. Areas of application of ion-sensitive field effect transistors for the continuous detection of concentrations are process measurement technology, analytical chemistry, industrial process monitoring or environment monitoring, wherein measurements are usually performed in aqueous solutions or organic mixtures. Aspects of particular importance are a highly precise concentration detection and a minimum long-term drift of the sensor in connection with acceptable costs.

Measurements of ionic concentrations in aqueous media are traditionally performed with glass electrodes both in process measurement technology and in laboratory measurement technology. In many aggressive media, it is possible to operate the glass electrodes stably, but in strongly alkaline solutions, their stability is limited.

Further, glass electrodes are usually not employed in hydrofluoric acid. The adjusting of the measurement value occurs very slowly. When they are manufactured, glass electrodes require a high percentage of manual labor making them expensive. Further, the area of application of glass electrodes is limited, because they produce chippings when breaking. For example, it is not possible to employ glass electrodes in food technology, because the chippings that result from breaking represent dangerous foreign bodies in food. Glass electrodes are preferably used in process measurement technology.

Further, due to technical reasons, particularly because a correspondingly large internal buffer volume is required, analogously to a reference electrode, with a sufficiently designed internal drain, mostly an Ag/AgCl arrangement, there is no possibility of efficient miniaturization of the glass electrodes. In the case of an ion-sensitive field effect transistor, the internal buffer and this second drain system are eliminated.

In addition, due to the necessary glass membrane thickness, the pH measurement system based on glass electrodes is a system with a high impedance and thus sensitive to environmental interferences. Therefore, the measurement lines should always be shielded and the distance of the electrodes should be kept at a minimum.

In contrast to the glass electrodes, the use of ion-sensitive field effect transistors represents a break-proof alternative to the ion-sensitive measurement in liquids so that they may be employed in areas where there are required additional operational safety requirements, such as in food technology. The application of the ion-sensitive field effect transistors for ionic concentration measurement, particularly for the measurement of the pH value, has been known for a long time, see for example P. Bergveld, IEEE Trans. Biomed. E17 (1979), p. 70. These sensors are further suitable for the miniaturization of the measurement system, the production of integrated systems and for a cost-effective production, and are superior to the conventional glass electrode in these respects.

Typically, when measuring with an ion-sensitive field effect transistor, its gate is brought in contact with the measured fluid. A change in potential at the gate caused by a change of an ionic concentration in the measured fluid results in a measurement signal. As the gate comes in direct contact with the measured liquid during the measurement, gate materials have to be used for the application in aggressive media, when high long-term stability and/or a low drift are required, which are resistant to the respective measured medium for long periods of time.

For producing hydrogen ion-sensitive layers, various materials such as $Si_3N_4$, $Al_2N_3$, $ZrO_2$, $Ta_2O_5$ and diamond-like carbon (DLC) have already been examined. For descriptions of such sensors, see, for example, Van der Schoot et al., Sensors & Actuators 4 (1983), p. 267, D. Sobczynska et al., Sensors & Actuators 6 (1984), p. 93, M. Klein et al., VDI-Berichte 509 (1983), p. 275, and T. Sakai et al., Internat. Electron Devices Meeting, Techn. Digest (1987), p. 711.

Ion-sensitive field effect transistors with a gate of $Si_3N_4$ are suitable for use in the above requirements only in a limited way, because the gate of $Si_3N_4$ is subjected to a high drift and exhibits low long-term stability. Further, the ion-sensitive field effect transistors with a gate of $Si_3N_4$ cannot be used in an aggressive media for longer periods of time.

Compared to $Si_3N_4$ as gate material, the use of metal oxides as gate material allows to achieve improved properties of ion-sensitive field effect transistors with respect to pH sensitivity, long-term stability, photosensitivity and drift.

Due to the crystalline structure of the metal oxides after thermal stress, the settling times of these sensors are larger as compared to the ion-sensitive field effect transistors of usually amorphous $Si_3N_4$. Ion-sensitive field effect transistors with a metal oxide gate further have the disadvantage that they do not have sufficient resistance to alkaline solutions at higher temperatures and hydrofluoric acid. Further, thermal treatments of metal oxides are performed in prior art for improving the chemical stability of an ion-sensitive field effect transistor on metal oxide basis. This forms crystalline modifications, causing, however, weak spots at the grain boundaries, which, in turn, favor ionic indiffusion which may increase drift or degrade photosensitivity.

Recent developments use ion-sensitive field effect transistors in which amorphous diamond-like carbon (DLC) is used as gate material, which has a high percentage of $sp^3$-hybridized carbon bonds. Such systems have very high chemical resistance, particularly in hydrofluoric acid. One disadvantage of using amorphous diamond-like carbon is, however, that layers of this material have a high internal stress which reduces layer adhesion and may result in the layers peeling off and the consequent destruction of the ion-sensitive field effect transistor. Furthermore, phase boundaries may result in long settling times of the measurement signal. Therefore, these ion-sensitive field effect transistors are not suitable for long-term use in all areas of application.

For the production of stable transistors, the layer materials used in prior art require a double-layer system in the channel consisting of $SiO_2$ and the sensitive layer to achieve a stable interface to silicon provided with minimal charge centers. This is associated with an increased production effort for the sensor chips and, due to the critical interfaces, a reduced yield.

SUMMARY OF THE INVENTION

It is the object of the present invention to provide a low-cost, safe and long-term stable ion-sensitive field effect transistor and a method for producing the same.

The present invention provides an ion-sensitive field effect transistor having a gate of metal silicate.

Further, the present invention provides a method for producing an ion-sensitive field effect transistor, comprising:
providing a substrate having a source region (14) and a drain region; and
generating a gate of metal silicate on the substrate.

In accordance with a first aspect, the present invention provides a field effect transistor for measuring an ionic concentration having a gate of metal silicate, wherein the gate either has only a layer of metal silicate as dielectric layer and ion-sensitive layer or wherein the gate has a layer of metal silicate as ion-sensitive layer, a dielectric layer of another material being formed between the ion-sensitive layer and the channel region.

In accordance with a second aspect, the present invention provides a method for producing a field effect transistor for measuring an ionic concentration, having the steps of providing a substrate having a source region and a drain region; and generating a gate of metal silicate on the substrate, wherein the gate either has only a layer of metal silicate as dielectric layer and ion-sensitive layer, or wherein the gate has a layer of metal silicate as ion-sensitive layer, a dielectric layer of another material being formed between the ion-sensitive layer and the channel region.

The present invention is based on the finding that an ion-sensitive field effect transistor with high stability and high sensitivity as well as low drift at good long-term stability is achieved by using metal silicate as gate material. The stability and sensitivity to an ion to be detected which are obtained by the use of metal silicate as gate material are comparable to those of metal oxides.

One advantage of the inventive ion-sensitive field effect transistor is that there is little transverse sensitivity, particularly with respect to alkali ions. Due to the structural properties of the metal silicates, expressed by a larger band gap as compared to metal oxides, less UV light-induced drift is caused.

By using metal silicates or metal silicate compounds, especially the silicates of hafnium and zirconium, there is further achieved high chemical stability of the ion-sensitive field effect transistor.

The increased chemical stability as compared to an ion-sensitive field effect transistor having a gate of metal oxide is the result of the high bonding strength of the metal silicate, expressed by the free enthalpy and the band gap.

Due to the high chemical stability, sensors having a metal silicate gate are provided with a broad range of applications, for example in the pH measurement technology.

Unlike the known ion-sensitive field effect transistors having a gate of $Si_3N_4$, metal oxide or diamond-like carbon, in which a double-layer structure is required in the transistor channel with an isolating layer and a sensitive layer, the use of metal silicates, and particularly of hafnium silicate and/or zirconium silicate, as sensitive layer allows to thin out significantly or do completely without the isolator layer $SiO_2$ below the sensitive layer which would otherwise be necessary. The production of a stable ion-sensitive field effect transistor having these materials according to the simple technology is based on the impurity-free transition from silicon to metal silicate.

Further, the use of metal silicates as gate material does not only achieve improved sensor properties, but also good reproducibility of the transistor parameters. The reproducibility of the transistor parameters is decisive for the application of the ISFET sensors. Thereby, the ion-sensitive field effect transistor on metal silicate basis may be achieved as a low-cost, highly stable sensor, for example for the use in industrial process measurement technology and environment monitoring.

Furthermore, while maintaining the chemical stability of the sensitive layer, the operating point of the sensor may be set such that the ionic movement in the electrical field is minimized during sensor operation. This further reduces the field-supported induffision of ions into the gate isolator. The embodiment with a single layer construction over the channel allows a reproducible sensor without interfering interface comprising a minimum of settling time.

The transistor parameters determine the operating point position of the sensor and the spread of the sensor parameters. The basis of homogeneous transistor parameters is the control of the isolator interfaces to silicon and, in the case of multiple layers, between the layers. The possibility of producing single layers therefore eliminates the critical interfaces of multiple layers. The interface exclusively dominant in the single layer gate isolator is the one of silicate to silicon. In the case of the metal silicate, it is characterized by the similarity of the atomic bonding states of the silicate with the amorphous $SiO_2$ resulting in interfaces which are formed largely free of stress and defects.

On the other hand, the silicates of zirconium and hafnium are thermodynamically stable in contact with $SiO_2$ and silicon so that there is no formation of silicide. This improves both drift and chemical stability.

Furthermore, the variability of the ratio of metal to silicon in the silicates allows generating layers with crystalline to amorphous structure. This can improve the response of the sensors as compared to that of metal oxide ion-sensitive field effect transistors.

The ion-sensitive field effect transistor realized in a single layer construction further reduces the required number of substeps in the production process, thus lowering production costs.

In this embodiment, the number of interfaces may thus be reduced, wherein there is the possibility to implement the layer over the channel in less thickness. This achieves a simple and low-cost production.

Generating the gate of metal silicate on the substrate may be done by sputtering or CVD depositing or vapor depositing of the metal silicate, by sputtering or CVD depositing or vapor depositing of a metal with subsequent silicatizing of the metal, or by sputtering or CVD depositing or vapor depositing of a metal with subsequent siliconizing of the metal and subsequent oxidizing.

Further, there may be performed tempering for adjusting sensor properties or some other post-treatment for adjusting a structural property of the gate. The tempering may be performed at temperatures higher than 500° C. under inert atmosphere, such as under $N_2$ pr noble gases and/or with oxidizing gas components. The structural property of the gate may thus be adjusted to a predetermined property between amorphous and crystalline.

Preferably, the layer production in semiconductor processes is performed by means of a CMOS-compatible technology, i.e. for example a planar technology, wherein further circuit elements integrated on the chip, which are for example used for detecting measurement data, may be generated together with the ion-sensitive field effect transistor. This achieves a low-cost production. A further advantage of the present invention is that the inventive ion-sensitive field effect transistor may be operated in a safe manner, i.e. without a risk of generating chippings when breaking, whereby it is suitable for areas of application requiring high operational safety, such as food technology.

The inventive ion-sensitive field effect transistor having a gate of metal silicate is further environmentally compatible, i.e. its use for example in food technology is possible without problems.

BRIEF DESCRIPTION OF THE DRAWINGS

Preferred embodiments of the present invention will be explained in more detail in the following with respect to the accompanying drawing, in which.

DESCRIPTION OF THE PREFERRED EMBODIMENTS

Figure 1:
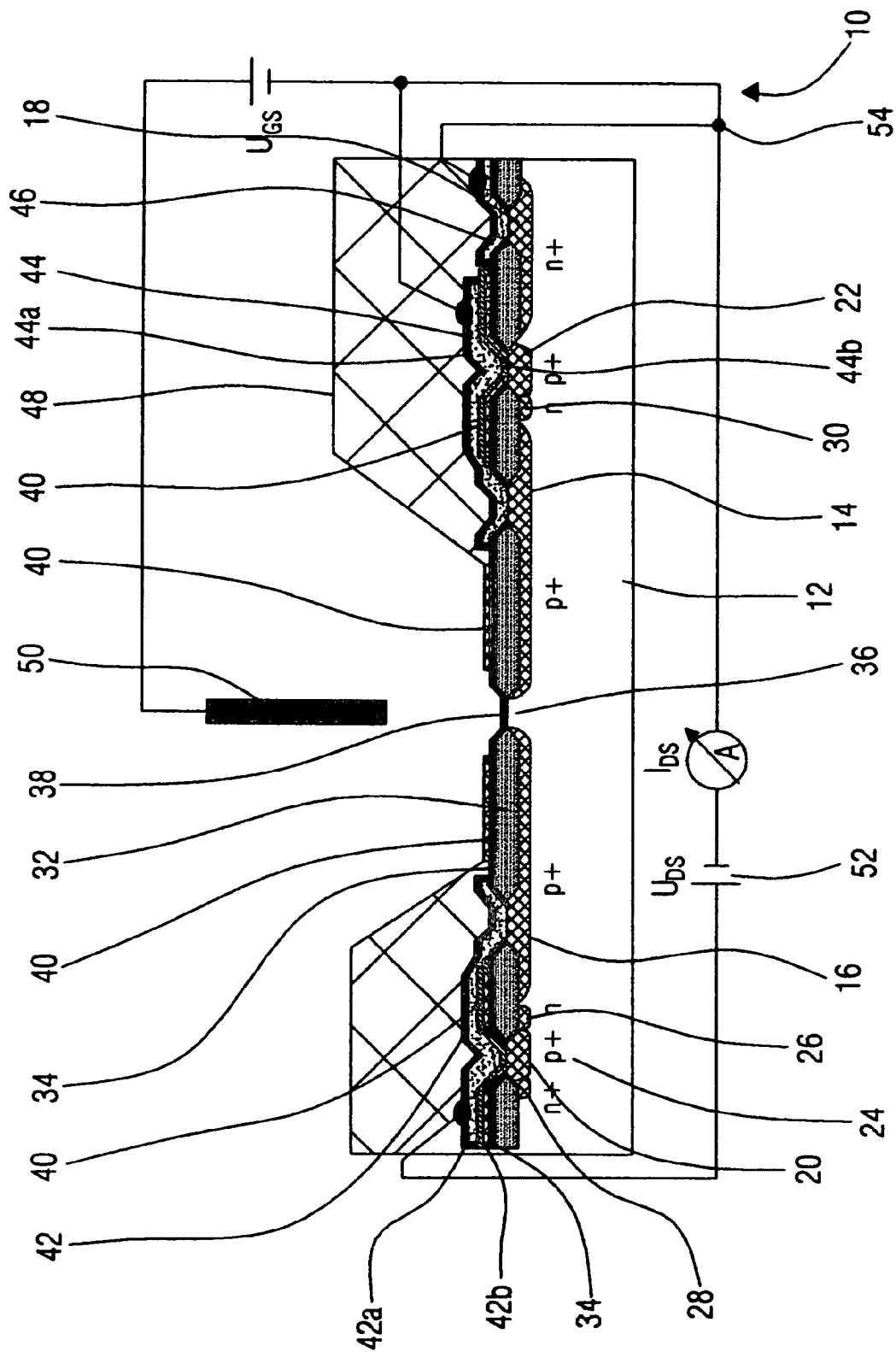
FIG. 1 shows a cross-sectional illustration of an ion-sensitive field effect transistor according to a preferred embodiment of the present invention.

FIG. 1 shows an ion-sensitive field effect transistor (FET) according to an embodiment of the present invention. The FET 10 includes a semiconductor substrate 12, for example a silicon substrate. The substrate 12 may be a combination of a carrier substrate and an epitaxy layer applied thereon, in which the active regions of the device are formed.

A $p^+$ source region 14 and a $p^+$ drain region 16 are formed in the substrate 12. In the substrate 12, there is further formed a substrate terminal region 18 comprising $n^+$ doping for forming an ohmic contact.

The substrate 12 further includes $p^+$ regions 20 and 22 respectively serving for forming an active bipolar device. The $p^+$-doped region 20 represents a base region of a bipolar transistor 24. The bipolar transistor 24 comprises an n-doped collector region 26 and an $n^+$-doped emitter region 28 respectively located on the sides of the base region 20.

Further, the $p^+$-doped region 22 and an n-doped region 30 adjacent to the same represent a diode as a further bipolar device on the substrate 12.

A field oxide layer 32 is formed on a surface of the substrate 12. On the field oxide layer 32A, there is arranged a gate layer 34 which further extends across a channel region 36 formed between the source region 14 and the drain region 16. A portion of the surface of the substrate 12 above the channel region 36 is exposed, i.e. the same is not covered by the field oxide layer 32. In this exposed region, a gate 38 comprising metal silicate according to the invention is formed by the gate layer 34, which, in this embodiment, is arranged directly on the channel region.

The use of metal silicate as gate material allows to produce the field effect transistor with a single layer in the channel region in this embodiment. This means that there is only the layer of metal silicate between the measured liquid and the channel region. Here the layer of metal silicate is both the gate isolator and the sensitive layer.

A further isolating layer 40 is further formed on the gate layer 34 in the regions of the field oxide layer 32. The field effect transistor 10 further includes a terminal contact 42, for example of aluminum, which extends through the field oxide layer 32 and the isolating layers 34 and 40 and is connected to the drain region 16 and the base region 20. The terminal contact 42 includes a first contact layer 42b and a contact layer 42a arranged above it. The first contact layer 42b provides a good electrical connection to the regions 16 and 20, while the contact layer 42a arranged above it ensures good solderability for electrical terminals.

Furthermore, the ion-sensitive field effect transistor 10 includes a second terminal region 44, also having two layers 44a and 44b extending through the field oxide layer 32 and the isolating layers 34 and 40 so that the second terminal region 44 is connected to the source region 14 and the region 22.

A third terminal region 46 is further connected to the substrate terminal region 18.

A protective layer 48 is formed over the terminal contacts 42, 44 and 46 in order to achieve an electrical isolation of the same with respect to the measured medium when immersing the ion-sensitive field effect transistor in a measured medium. Furthermore, the protective layer 48 provides a mechanical protection for the terminal contacts 42, 44 and 46.

The field effect transistor having a gate 38 of metal silicate exhibits a higher chemical stability as compared to a gate of metal oxide due to the high bonding strength.

Thus the gate 38 of metal silicate exhibits high resistance to chemically aggressive substances so that the ion-sensitive field effect transistor 10 may be operated with high durability in aggressive chemical media, such as hydrofluoric acid. Furthermore, the inventive ion-sensitive field effect transistor is characterized by a high long-term stability and low drift.

In the above field effect transistor 10, a single layer gate construction is used, i.e. the gate layer 34 forming the gate 38 in the channel region 36 is both the gate isolator and the sensitive layer.

Preferably, hafnium silicate and/or zirconium silicate are used as material for forming the gate layer 34, because they are characterized by a particularly high chemical stability.

Using silicates further eliminates the disadvantageous properties of increased drift and low photosensitivity generated by the thermal treatment particularly in ion-sensitive field effect transistors having a metal oxide gate.

Preferably, the inventive ion-sensitive field effect transistor is produced in a CMOS process, which allows a low-cost production of the same. Typically, several ion-sensitive field effect transistors are produced in a wafer arrangement on 150 mm semiconductor wafers. Then chips comprising for example an area of about 4 mm×4 mm are mounted separately to boards and are electrically contacted. For producing a measurement system, a chip is then transferred to a suitable construction. Typically, a measurement system where the ion-sensitive field effect transistor is installed represents an immersion sensor, which may be used, for example, for detecting a pH value in industrial sewage.

In preferred embodiments of the present invention, the gate layer of metal silicate is produced by sputtering the metal, the metal oxide or the metal silicate in an oxygen-$Si_xH_y$ atmosphere, or by CVD deposition. For annealing and modifying the layer properties, a thermal treatment may then be performed at temperatures which are higher than 500° C., wherein this may be performed under inert atmosphere or with oxidizing gas components.

In the following, there will be explained an example of the use of the inventive ion-sensitive field effect transistor. In this example, an ionic concentration measurement is performed using the ion-sensitive field effect transistor. For this, the field effect transistor 10 is brought into contact with a measured liquid, which may, for example, be an aqueous solution. Further, a reference electrode 50 which, for example, may consist of Ag/AgCl/KCl, is inserted into the measured medium for the measurement. A drain-source current IDS is caused via a voltage source 52 connected to the terminal contacts 42 and 44 to apply an electrical voltage $U^{dS}$ between the source region 14 and the drain region 16. The terminal contact 18 is on a reference potential 54, for example ground.

Due to a different electrochemical voltage valency of the materials of the reference electrode 50 and the gate 38, an electric voltage is formed between the reference electrode 50 and the gate 38 depending on an ionic concentration of the measured medium.

In a preferred embodiment, the voltage source 52 is formed to control the drain-source voltage so that there is always a constant drain-source current. In this embodiment, the gate potential is consequently determined and adjusted by the constant drain-source current for a changing ionic concentration. When the ionic concentration of the measured medium changes, the potential of the reference electrode 50 with respect to ground changes due to the changing electric voltage between the reference electrode 50 and the gate 38. Here, the voltage $U_{GS}$ applied between the source and the reference electrode 50 represents a measurement quantity depending on an ionic concentration of the measured medium, whereby the concentration of the measured medium may be determined by sampling the voltage $U_{GS}$.

Although the described embodiments only described a field effect transistor having a p-substrate, n-source region and n-drain region, the present invention is not limited thereto, but also includes field effect transistors having an n-substrate, p-source region and p-drain region.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. An ion sensitive field effect transistor for measuring an ion concentration of a fluid comprising:
   a source region, a drain region, and a channel region between the source region and the drain region; and
   a gate formed above the channel region;
   wherein the gate either comprises only a layer of metal silicate as dielectric layer and ion-sensitive layer or wherein the gate comprises a layer of metal silicate as ion-sensitive layer, a dielectric layer of another material being formed between the ion-sensitive layer and the channel region; and
   wherein said ion-sensitive layer is arranged to be exposed to said fluid to be measured.

2. The ion-sensitive field effect transistor of claim 1, wherein the gate comprises zirconium silicate.

3. The ion-sensitive field effect transistor of claim 1, wherein the gate comprises hafnium silicate.

* * * * *